United States Patent [19]

Okuyama et al.

[11] Patent Number: 5,549,123

[45] Date of Patent: Aug. 27, 1996

[54] PROCESS FOR PRODUCING BIOCOMPATIBLE IMPLANT MATERIAL BY FIRING A MIXTURE OF A GRANULATED POWDER AND A COMBUSTIBLE SUBSTANCE

[75] Inventors: Masahiko Okuyama; Kohji Okada; Katsuya Yamagiwa, all of Aichi, Japan

[73] Assignee: NGK Spark Plug Co., Ltd., Nagoya, Japan

[21] Appl. No.: 366,305

[22] Filed: Dec. 29, 1994

[30] Foreign Application Priority Data

Dec. 29, 1993 [JP] Japan ................................. 5-353488

[51] Int. Cl.$^6$ ................................................ A61B 19/00
[52] U.S. Cl. ............................ 128/898; 623/16; 623/901; 433/201.1
[58] Field of Search ................. 623/16, 901; 433/201.1; 128/898; 264/44, 59

[56] References Cited

U.S. PATENT DOCUMENTS

| 4,179,485 | 12/1979 | Tritten | 623/16 |
| 4,737,411 | 4/1988 | Graves, Jr. et al. | 623/16 |
| 4,891,174 | 1/1990 | Seki et al. | 264/44 |
| 5,064,436 | 11/1991 | Ogiso et al. | 623/16 |
| 5,266,248 | 11/1993 | Ohtsuka et al. | 623/16 |

FOREIGN PATENT DOCUMENTS

60-50744  11/1985  Japan.

*Primary Examiner*—Paul Prebilic
*Attorney, Agent, or Firm*—Sughrue, Mion, Zinn, Macpeak & Seas

[57] ABSTRACT

A biocompatible implant material is disclosed comprising (i) particles connected each other and (ii) vacant spaces comprising three-dimensionally interconnected pores present among the particles, wherein the particles have an average size of 10 to 800 μm and the pores have a size of 2 to 800 μm, and the process for producing the biocompatible implant material which comprises granulating a raw powder having an average particle size of 5 μm or smaller to give raw granules having an average particle size of 10 to 800 μm, mixing the raw granules with a combustible substance having an average particle size of 2 to 1,600 μm, pressing the mixture into a shape at a pressure of 1 to 100 kg/cm$^2$, and then firing the shape.

10 Claims, 8 Drawing Sheets

PRIOR ART

PROCESS FOR PRODUCING BIOCOMPATIBLE IMPLANT MATERIAL BY FIRING A MIXTURE OF A GRANULATED POWDER AND A COMBUSTIBLE SUBSTANCE

FIELD OF THE INVENTION

The present invention relates to a biocompatible implant material and a process for producing the same. The biocompatible implant material of the present invention is suitable for use as an artificial bone compensation material in medical fields such as orthopedics, plastic surgery, cerebral surgery, oral surgery, and dental surgery.

BACKGROUND OF THE INVENTION

Biocompatible implant materials made of metal have conventionally been used. In recent years, however, ceramics are attracting attention from the standpoint of biocompatibility, and ceramic implant materials have been put to practical use. In particular, calcium phosphate compounds have excellent biocompatibility, and sintered bodies obtained therefrom are known as a material which chemically bonds to a bone or is replaced by a bone.

The present inventors have already proposed in JP-B-60-50744 (the term "JP-B" as used herein means an "examined Japanese patent publication") a process for producing a calcium phosphate sintered body having good biocompatibility and high strength which process comprises incorporating an alkaline earth metal oxide/phosphoric acid frit into a powder consisting mainly of a calcium phosphate having a calcium atom/phosphorus atom ratio of from 1.4 to 1.75, followed by firing, the amount of the frit being 0.5 to 15% by weight based on the amount of the resulting calcium phosphate sintered body. This process succeeded in producing biocompatible implant materials having excellent biocompatibility and high mechanical strength. These implant materials, when implanted in living bodies, chemically bonded to bone tissues and did not readily fracture due to their high strength, giving satisfactory results. However, bone growth on these implant materials was insufficient because bone tissues did not penetrate into the implant materials. As a result, much time was required for bone tissues to adhere to the implant materials.

On the other hand, porous implant materials have excellent biocompatibility although inferior in strength to dense materials. In particular, porous implant materials having pores as large as from tens to hundreds of micrometers are known as a material into which bone tissues readily penetrate. Known methods for producing porous objects include the technique of incorporating a combustible pore-forming material, e.g., an organic substance or carbon, into a raw material and the technique of incorporating a foaming agent or the like. These techniques have long been employed for the production of bricks and other products. If these techniques are applied to a calcium phosphate material, porous objects for implantation may be produced.

However, the porous biocompatible implant materials produced by such conventional techniques frequently have shown insufficient bone growth because the penetration of bone tissues into pores thereof does not occur, even though the implant materials are a porous calcium phosphate object having pores as large as, e.g., about 100 µm.

Such conventional porous objects have had another drawback because of the significantly low strength thereof. Specifically, touching or rubbing with a finger results in falling of particles or breakage, so that the porous-objects have very poor handleability in bone compensation surgery.

SUMMARY OF THE INVENTION

The present invention has been accomplished in order to eliminate such drawbacks.

An object of the present invention is to provide a biocompatible implant material which is excellent in biocompatibility, especially in initial bone growth, and has relatively high mechanical strength, by forming a pore structure comprising interconnected pores in which the narrowest parts thereof are regulated to have a diameter not smaller than a given value.

Another object of the present invention is to provide a process for producing the biocompatible implant material.

The biocompatible implant material of the present invention has a connected-particle structure in which particles having an average size of 10 to 800 µm are connected together, wherein the connected-particle structure has vacant spaces therein comprising three-dimensionally interconnected pores present among the particles and the pores have a size of 2 to 800 µm (i.e., have a size distribution of 2 to 800 µm).

The process of the present invention for producing the above biocompatible implant material comprises granulating a raw powder having an average particle size of 5 µm or smaller to give raw granules having an average particle size of 10 to 800 µm, mixing the granules with a combustible substance having an average particle size of 2 to 1,600 µm, pressing the mixture into a shape at a pressure of 1 to 100 kg/cm$^2$, and then firing the shape.

DETAILED DESCRIPTION OF THE INVENTION

Figure 2:
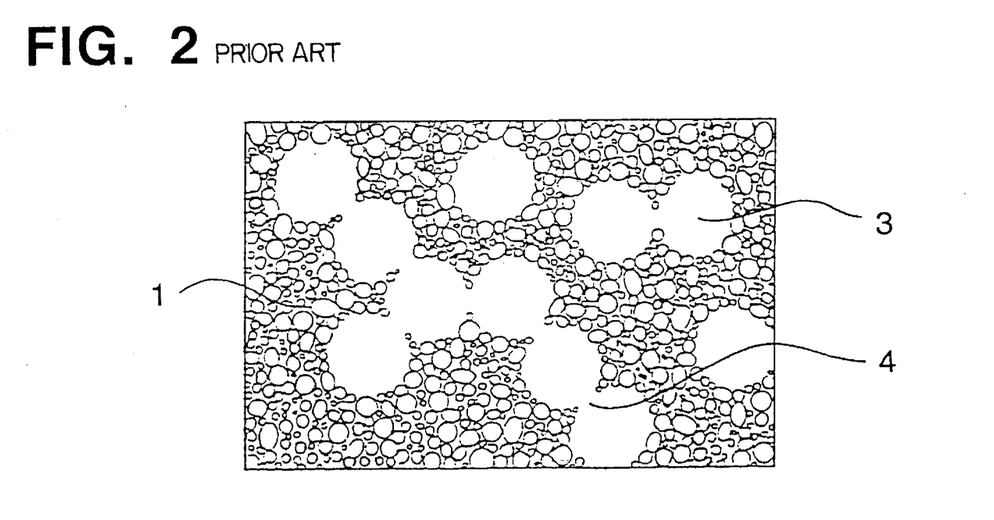
FIG. 2 is a schematic view illustrating a pore structure in a conventional biocompatible implant material.

The present inventors investigated the cause of the slow bone growth on a porous biocompatible implant material produced by the conventional technique. As a result, the following has been found. Even when a raw material containing combustible particles of, e.g., 100 µm is used to produce a porous implant material, the pores formed through firing are either present apart from one another or narrowly connected to one another through point contacts, as illustrated in FIG. 2. That is, in the pore structure in such a porous implant material, extremely narrow vacant parts (point contact parts) are intermittently present in each continuous space formed by the interconnection of pores. The slow bone growth may be therefore attributable to the presence of such narrow parts, which inhibit the penetration of bone tissues.

The most significant feature of the biocompatible implant material of the present invention resides in the pore structure having vacant spaces therein comprising three-dimensionally interconnected pores (through-pores) present among particles of a connected-particle structure and having a size of 2 to 800 µm. These pores not only are interconnected open pores with a large size, but also have no extremely narrow parts which inhibit bone tissue penetration. Because of this, the penetration of bone tissues is very easy and the implant material of this invention shows high biocompatibility.

Figure 1:
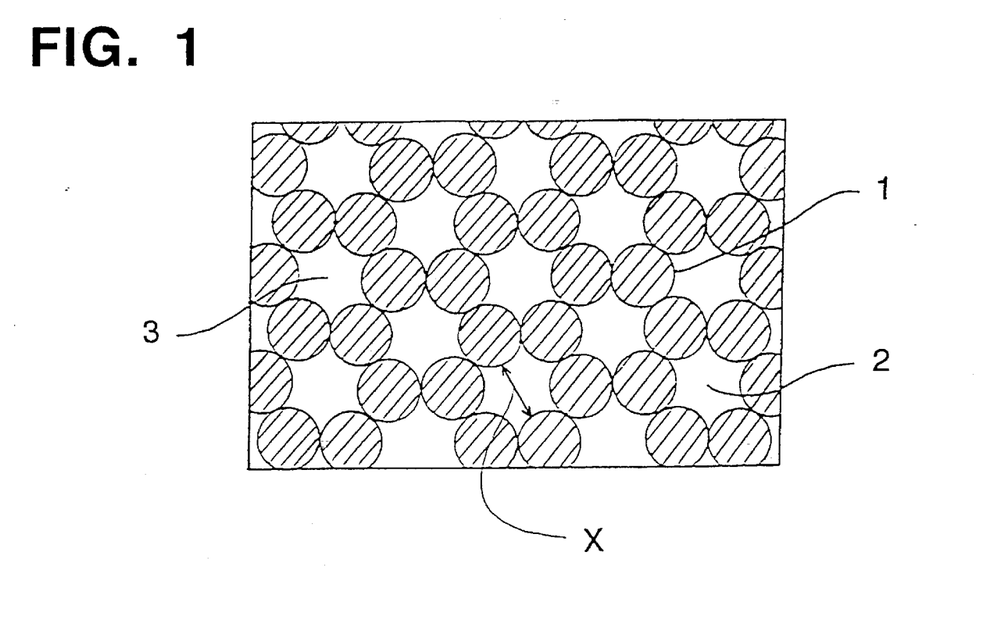
FIG. 1 is a schematic view illustrating a pore structure in a biocompatible implant material of the present invention.

The pore size is an interval (x) as shown in FIG. 1 between the particles faced each other in the direction perpendicular to the interconnected pore direction, the interval being measured with an ordinary scanning electron microscope.

The specific pore structure has been found to be formed by preparing nearly spherical raw granules from a raw powder, mixing the raw granules with combustible dummy particles, compacting the mixture into a shape in an almost closest-packing state without breaking the granules, and then firing the shape. Through the firing, the combustible dummy particles are burned out to leave vacant parts, and the individual vacant parts are connected to adjacent ones while maintaining relatively large pore sizes to form interconnected pores. As a result, a pore structure is obtained which has no extremely narrow parts with a size below 2 µm at the joints between such pores. Another major feature is that the implant material of the invention has a higher mechanical strength than conventional porous objects having the same porosity, because the nearly spherical granules were compacted into the closest-packing state and neck growth through firing is satisfactory.

Such a pore structure can be easily obtained by the process of the present invention, although difficult to obtain with any conventional process for producing a porous object.

The reasons for the average particle size limitation to 10 to 800 µm in the biocompatible implant material described above are as follows. If the particle size is smaller than 10 µm, satisfactory pores are less apt to form, resulting in poor biocompatibility. If the particle size is larger than 800 µm, the implant material has so low strength that particles fall off even upon rubbing with a finger, i.e., the implant material has extremely poor handleability. In the present invention, the particle size is the average of the longer axis (l) and the shorter axis (s), (l+s)/2, measured with a scanning electron microscope.

The particles may have an irregular shape or a shell-shape such as granulated ones which are prepared by pressing a powder, loosening and screening the pressed powder. However, the nearly spherical shape of the particles is preferred in that nearly spherical particles are satisfactorily packed to attain good interparticulate contact and neck growth between particles occurs readily during firing, resulting in a biocompatible implant material having high strength and excellent handleability. The particles desirably have open fine pores with a size of 2 µm or smaller because the presence of such open fine pores further improves bonding with bone tissues.

In the present invention, "nearly spherical (shape)" means that the ratio of the longer axis (l) to the shorter axis (s) of a particle, l/s, is close to 1, more specifically, in the range of $1 \leq l/s < 2$ and that the particle has a regular shape.

The material of the particles is not particularly limited, but ceramics are preferred from the standpoint of biocompatibility. Preferred examples thereof include ceramics inert to the living body, such as alumina ceramics, zirconia ceramics, and alumina-zirconia ceramics, and calcium phosphate ceramics including hydroxyapatite and calcium tertiary phosphate. It is a matter of course that these ceramics may contain a sintering aid, e.g., silica, magnesia, calcia, or yttria, a glass, or other component besides the main component, i.e., alumina, zirconia, etc. The most desirable is a material comprising a mixed phase consisting of hydroxyapatite and calcium tertiary phosphate, which material has exceedingly high biocompatibility. The weight ratio of calcium tertiary phosphate to hydroxyapatite is not limited (i.e., from 0 to 100%), however, preferably from 10 to 50% from the standpoint of biocompatibility.

The reason for the use of a raw powder having an average particle size of 5 µm or smaller in the process for producing the above-described biocompatible implant material is as follows. If a raw powder having an average particle size exceeding 5 µm is used, neck growth is less apt to occur within and between particles and a porous object having a connected-particle structure is not obtained. As a result, the sintered body obtained suffers particle falling, that is, it does not have the strength desired for biocompatible implant materials. It is more desirable to employ a raw powder having an average particle size of 3 µm or smaller because higher strength is attainable.

The raw powder described above is first granulated to give raw granules having an average particle size of 10 to 800 µm. Methods for the granulation are not particularly limited. For example, use may be made of a method in which the raw powder is first pressed by dry pressing and the pressed body is crushed and screened to obtain granules of a desired particle size. However, a spray drying method using a spray dryer is most desirable. This method yields raw granules having a nearly spherical shape, which can be packed extremely satisfactorily and from which a connected-particle structure can be easily obtained. Specifically, an organic binder, e.g., poly(ethylene oxide) (PEO) or an emulsified acrylic binder, is added to the raw powder along with a dispersant, water, etc. to give a slurry having a viscosity of 5 to 30 cP, and this slurry is spray-dried to produce granules having an average particle size 20 to 800 µm. The organic binder added to the raw powder is generally used in an amount of 1 to 5 wt % based on the raw ceramics contained in the raw powder. The dispersant added to the raw powder is generally used in an amount of 0.5 to 2 wt % based on the raw ceramics contained in the raw powder. By controlling the operation conditions for the spray dryer (slurry concentration, rotational speed of the spindle, drying temperature, etc.), the particle size of raw granules can be regulated so as to be suited for the structure of the biocompatible implant material to be produced. The raw granules obtained are subjected to screening to obtain granules of a preferred particle size. Although there are cases where the raw granules have voids with a size of several micrometers to tens of micrometers or larger depending on spray drying conditions, such granules can be used as they are.

The combustible substance for use in the present invention is indispensable to the formation of the pore structure characteristic of the present invention, and is not particularly limited as long as it is an organic substance which can be burned out during the firing step, for example, carbon and granulated sugar, etc. may be widely used. However, nearly spherical (close to sphere) organic beads of acrylic or polystyrene resin such as PMMA are preferred because they show satisfactory filling property with raw granules and a satisfactory connected-particle structure is easily formed. Further, these organic beads are secure against the destruction of the sintered bodies because the combustion reaction thereof is not so rapid compared to carbon, etc.

The reasons why the combustible substance should have an average particle size of 2 to 1,600 μm are as follows. If the average particle size thereof is smaller than 2 μm, vacant spaces comprising three-dimensionally interconnected pores having a size of 2 μm or larger are not obtained, only resulting in an increased porosity. On the other hand, the average particle size larger than 1,600 μm are undesirable in that use of such raw granules results not only in poorly interconnected pores and an unsatisfactory pore structure, but also in extremely large pores with a size exceeding 1,000 μm, that is, the implant material thus produced has significantly reduced strength and suffers particle falling or breakage even upon touching with a finger.

The volume ratio of the combustible substance to the raw granules is generally from 10 to 60%. If the volume ratio thereof is less than 10%, the pore structure of the present invention is not sufficiently obtained. If that ratio is more than 60%, resistance to particle falling (strength) is lowered.

A nearly spherical shape is preferred for the raw granules and the combustible substance. This is because as the granules and the combustible substance become nearly spherical more and more, they come to be packed and contacted with one another in more satisfactory manner to give a sintered body having increased strength and a preferred pore structure.

The reasons why the ratio of the average particle size (S1) of the combustible substance to the average particle size (S2) of the raw granules (S1/S2) is from 0.2 to 5 are as follows. If that ratio is lower than 0.2, the incorporation of the combustible substance does not result in the formation of the specific pore structure having vacant spaces therein comprising three-dimensionally interconnected pores which are present among particles of the connected-particle structure characteristic of the present invention and have a size of 2 μm or larger, although effective in attaining an increased porosity. If that ratio is higher than 5, the pores formed are poorly interconnected, i.e., merely connected with one another through point contacts, so that the implant material obtained has poor biocompatibility with insufficient penetration of bone tissues and also has extremely low strength and very poor handleability. The preferred range of that ratio (S1/S2) is from 0.5 to 2.

After the raw granules and combustible substance described above are mixed, the mixture is pressed at a pressure of 1 to 100 kg/cm$^2$ with a mold press, rubber press, hydrostatic press, or the like. For obtaining a porous object with sufficient strength, it is desirable to press the raw granules and the combustible substance into a shape in a nearly closest-packing state without deforming or breaking the raw granules. The reasons why the pressing pressure of 1 to 100 kg/cm$^2$ is used are as follows. If a pressing pressure lower than 1 kg/cm$^2$ is used, the particles are insufficiently packed and neck growth during firing is insufficient, resulting in a porous object which has low strength and is hence apt to suffer particle falling, i.e., which has poor handleability and cannot withstand cutting operation. On the other hand, pressing pressures higher than 100 kg/cm$^2$ are undesirable in that the raw granules are crushed and deformed, resulting in a fired object having impaired pore interconnection and poor biocompatibility. The appropriate pressure for this pressing depends on the mechanical strength of the raw granules, i.e., the particle size of the raw powder and the conditions used for the preparation of the raw granules. However, the appropriate pressure can be easily determined by conducting a pretest using various pressures within the range of the invention. The pressing of the raw granules at such a pressure, which is lower than conventional ones, is preferred from the standpoint of forming a connected-particle structure because at such a low pressure the raw granules can be brought into dense and even contact with one another while avoiding granule crushing.

The shape obtained by pressing is then fired first at 100° to 500° C. to burn out the combustible substance and then at an elevated temperature to permit the necks within and between the raw granules to grow. As a result, interparticulate bonding proceeds to obtain the desired biocompatible implant material. The firing temperature depends on the composition of the material used. For example, alumina ceramics are fired at 1,200° to 1,650° C., zirconia ceramics at 1,100° to 1,800° C., alumina-zirconia ceramics at 1,200° to 1,700° C., and calcium phosphate ceramics at 900° to 1,400° C. If these materials are fired at a temperature lower than the respective temperatures specified above, neck growth between particles does not proceed, so that a biocompatible implant material having a connected-particle structure is not obtained. Firing temperatures higher than the temperatures specified above are also undesirable in that a connected-particle structure is formed but is then broken.

The pores according to the present invention may comprise (1)large pores present among particles, that is, three-dimensionally interconnected large pores having a size of 2 to 800 μm and (2)open fine pores present inside particles, that is, open fine pores having a size of 2 μm or smaller inside particles. The open fine pores inside particles are prepared by lowering the firing temperature to prevent raw granules from densifying. For example, in the case of using a calcium phosphate base in raw granules like Sample No. 31 of Example 1 below, the primary particles in the raw granules which are fired at a temperature of 1100° C. are not sufficiently densified each other to form pores therein having a size of 2 μm or smaller, while the inside of particles which are fired at a temperature of 1300° C. are almost densified to disappear the pores inside particles. In the 1300° C. firing, closed pores may just generated inside particles to a small amount.

An especially preferred raw material for use in forming a connected-particle structure in the process of the present invention is a material which comprises a mixture of a raw ceramic powder serving as the main component of the biocompatible implant material and a glass powder and which can be sintered by liquid-phase sintering. Preferred examples thereof include a mixture of a raw powder of hydroxyapatite and a powder of calcium phosphate glass. This powder mixture undergoes a chemical reaction during firing with the elimination of the glass powder particles to form either a mixed phase consisting of hydroxyapatite and calcium tertiary phosphate or a calcium tertiary phosphate phase, which phases each has excellent biocompatibility. During this firing, the glass powder particles form a liquid phase and greatly accelerate bonding (neck formation)

among the fine raw powder particles of hydroxyapatite and among the raw granules. As a result, a connected-particle structure comprising tenaciously connected particles is formed. This neck growth is a factor extremely important for attaining both a high porosity and a high mechanical strength. Although the desired biocompatible implant material can be obtained also from other raw powders, use of such other raw powders may necessitate stricter regulation of the pressing or firing conditions in order to attain sufficient neck growth during firing. The weight ratio of (A) a crystalline or glass powder which generates a liquid phase, that is, which melts to be soften, during firing to (B) a crystalline ceramic powder is from 0.1 to 30%. If the weight ratio of (A) powder to (B) powder is less than 0.1%, sufficient neck growth during firing is not obtained. On the other hand, if that ratio is more than 30%, the merits by forming neck are lost and the original characteristics of (B) powder is spoiled.

A brief explanation for the fact that the biocompatible implant material of the present invention has excellent biocompatibility is given below, although it still contains a conjecture.

As previously noted, the most significant feature of the biocompatible implant material of the present invention resides in the pore structure having vacant spaces therein comprising three-dimensionally interconnected pores present among particles of a connected-particle structure and having a size of 2 to 800 μm. These vacant spaces are made up of pores connected to one another while maintaining large pore sizes, and are hence utterly different from the conventional pore structure comprising large pores narrowly interconnected through narrow contact points.

Figure 7:
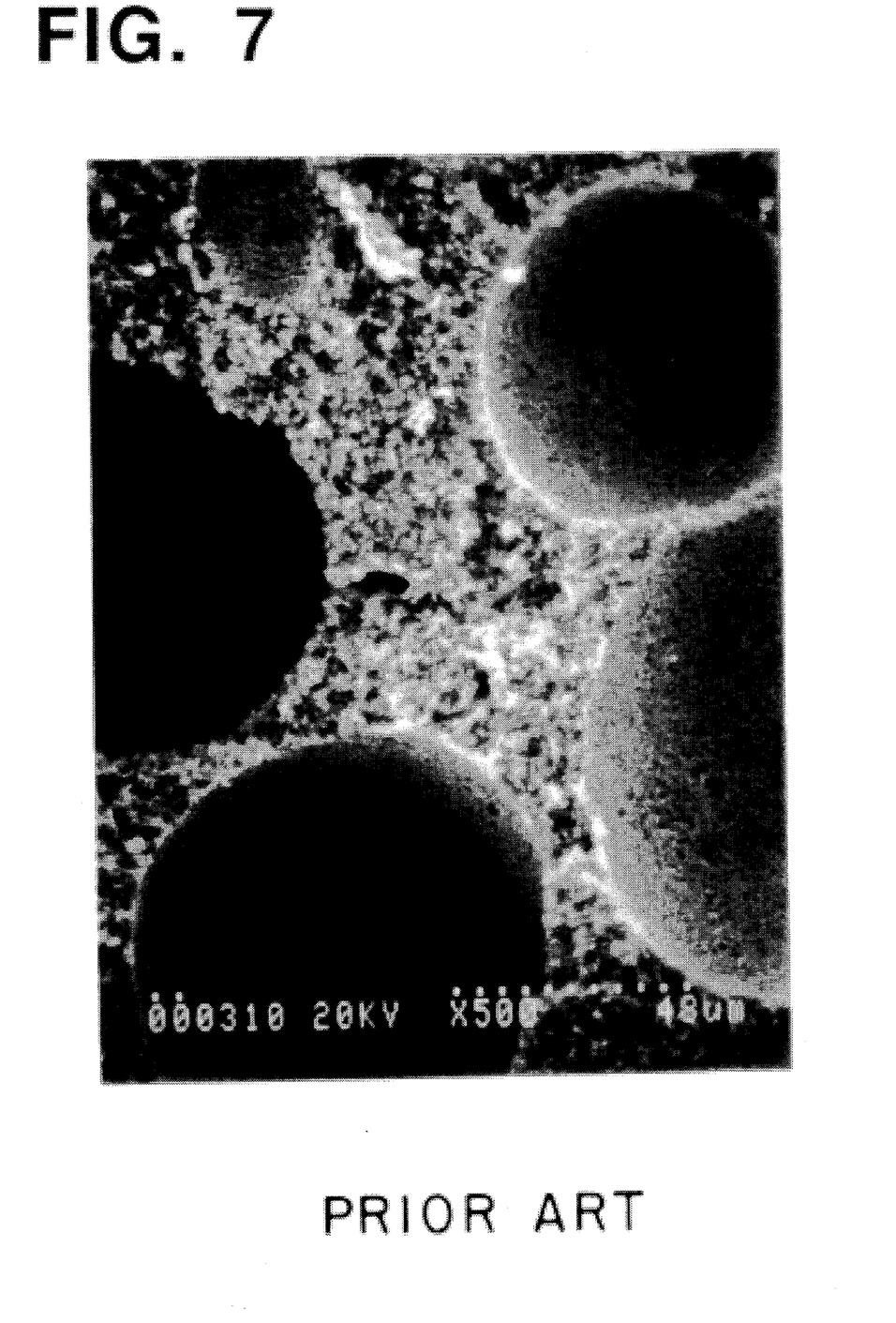
FIG. 7 is a scanning electron photomicrograph showing the microstructure of a biocompatible implant material obtained in Comparative Example 1.
Figure 8:
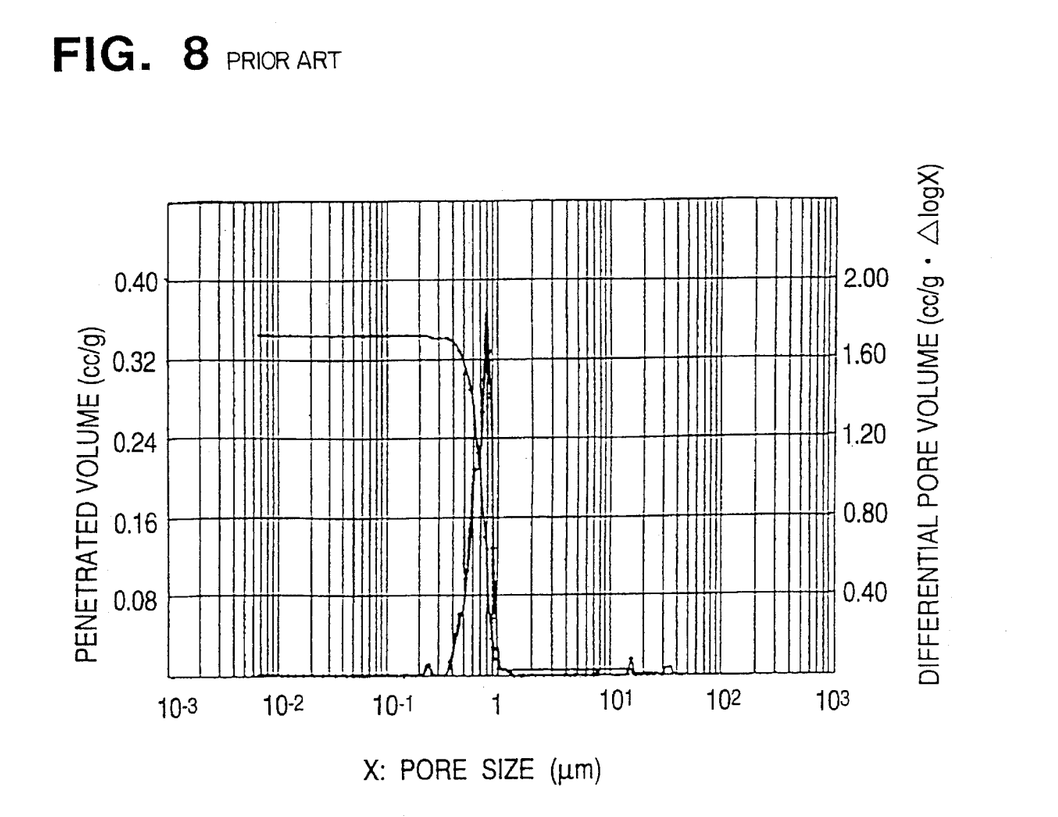
FIG. 8 is a chart showing the pore diameter distribution for a biocompatible implant material obtained in Comparative Example 1.

Such a difference in pore structure is made clear with a measurement by the mercury penetration method. In an examination for determining a pore size distribution by the mercury penetration method, a continuous pore in which the pore size is larger at an inner part than at any part on the entrance side is detected as a pore having the diameter corresponding to the narrowest part on the entrance side, because of the principle of the measurement. This is because the rate of the penetration of mercury into a pore is determined by the pressure in equilibrium with the size of the narrowest part of the pore (ink bottom effect). Consequently, a conventional porous object having narrow vacant parts as illustrated in FIG. 2 is characterized in that the pore diameters thereof as measured with an ordinary scanning electron microscope (hereinafter referred as "SEM") differ markedly from the pore sizes measured by the mercury penetration method. In FIG. 2, numeral 1 denotes a particle, 3 a pore, and 4 a pore joint. For example, as FIGS. 7 and 8 show, an examination of a conventional porous object with an SEM revealed the presence of pores having a size of nearly 100 μm, whereas in an examination by the mercury penetration method no 100 μm pores were observed and only pores of about 1 μm were observed. This is because since the pore structure of such a porous object produced by a conventional process, although having large pores inside, is extremely narrow at pore joints, a measurement by the mercury penetration method gives smaller pore-size values than by the SEM method. It is thought that these extremely narrow parts inhibit the penetration of bone tissues.

In contrast, the biocompatible implant material of the present invention has vacant spaces comprising three-dimensionally interconnected pores with a size of 2 to 800 μm as illustrated in FIG. 1. In FIG. 1, numeral 1 denotes a particle, 2 a vacant space and 3 a pore, and x denotes a pore size. Since the implant material of this invention has no extremely narrow pore parts such as those in the conventional porous object, the pore sizes measured with an SEM agree well with the pore sizes determined by the mercury penetration method. Due to such a pore structure, a body fluid penetrates extremely easily into vacant spaces of the implant material after implantation in a living body, thereby accelerating the growth of a new bone. Thus, high biocompatibility with excellent bone tissue penetration is attained.

The present invention will be explained below in more detail by reference to the following Examples, but the invention should not be construed as being limited thereto.

EXAMPLE 1

The following procedure was conducted according to the conditions shown in Tables 1 to 4. First, a hydroxyapatite powder having an average particle size of 0.6 μm was mixed with 5 wt % calcium phosphate glass frit (having a CaO-$P_2O_5$ content of 90 mol % or higher) to obtain a powder mixture as a raw powder. A poly(ethylene oxide) binder was added to the raw powder to prepare an aqueous slurry. This slurry was granulated with a spray dryer, and the granules were classified into four kinds of raw granules having average particle sizes of about 30 μm, 60 μm, 90 μm, and 300 μm, respectively. Each of spherical acrylic combustible substances having particle sizes of 7 μm, 20 μm, 60 μm, 130 μm, and 300 μm, respectively, was dry-mixed with the raw granules in given proportions. These mixtures each was pressed into a cylindrical sample with a diameter of 10 mm by the mold press method at various pressures of from 3.5 to 100 kg/cm². The pressed shapes thus obtained were heated in an electric furnace at a heating rate of 300° C./hr and fired therein at a temperature of 1,100° C. or 1,300° C. for 2 hours. Thus, samples Nos. 1 to 31 were obtained.

The classification of the raw granules was conducted by using 325-mesh, 200-mesh and 100-mesh screens to classify the following four sieve fractions.

(I) <325-mesh (<45 μm)
(II) 325-mesh to 200-mesh (45 to 75 μm)
(III) 200-mesh to 100-mesh (75 to 150 μm)
(IV) >100-mesh (>150 μm)

The average particle size and the particle size distribution of the raw granules were determined by measuring particle sizes of 100 granules of the four sieve fractions with an SEM. The resulting particle size distributions of the four sieve fractions are each narrow so that, even in the sieve fractions having an average particle size of 30 μm and 300 μm ((I) and (IV)), the raw granules having of not less than ½ time or not more than 2 times that of an average particle size of the whole raw granules account for 80% of the whole raw granules. In the sieve fraction having an average particle size of 30 μm (I), the raw granules having a particle size of 15 (=30×½) to 45 μm (corresponding to the value of the 325-mesh) account for 80% or more of the whole raw granules.

In the sieve fractions having average particle sizes of 60 μm and 90 μm ((III) and (IV)), the raw granules having of ½ to 2 times that of an average particle size of the whole raw granules account for 100% of the whole raw granules because of the mesh size used.

The acrylic combustible substances used as a combustible substance were organic beads commercially available. The particle size distributions thereof were narrow. For example, in the organic beads having an average particle size of 130 μm, the organic beads having a particle size of 50 to 500 μm account for 100% of the whole organic beads, and the organic beads having a particle size of ½ to 2 times that of an average particle size (65 to 260 μm) account for 80% or more of the whole organic beads.

Each of the samples obtained was examined for porosity, open-pore rate, pore size determined by the mercury penetration method, and particle falling, and further examined with an SEM. The porosity (total pore content based on total volume) and open-pore rate (open-pore content based on total pore content) of each sample were determined by measuring the true specific gravity (T), bulk specific gravity (B), and apparent specific gravity (A) of the sample and calculating the porosity and the open-pore rate from these found values in a known way. The porosity and the open-pore rate are defined by the following formulae, respectively:

$$(\text{porosity}) = \frac{(\text{total pore content})}{(\text{total volume})} = \frac{T-B}{T}$$

$$(\text{open-pore rate}) = \frac{(\text{open-pore content})}{(\text{open-pore content}) + (\text{closed-pore content})}$$
$$= 1 - (\text{closed pore rate})$$
$$= 1 - \frac{T-A}{T} / \frac{T-B}{T}$$

wherein T represents a true specific gravity, B represents a bulk specific gravity and A represents an apparent specific gravity. The results obtained are shown in Tables 2 and 4. Further, the surfaces of sintered bodies were examined by X-ray diffractometry to identify the crystalline phase thereof. As a result, the crystalline phase was found to be composed of a mixture of calcium tertiary phosphate and hydroxyapatite for each sample.

Figure 3:
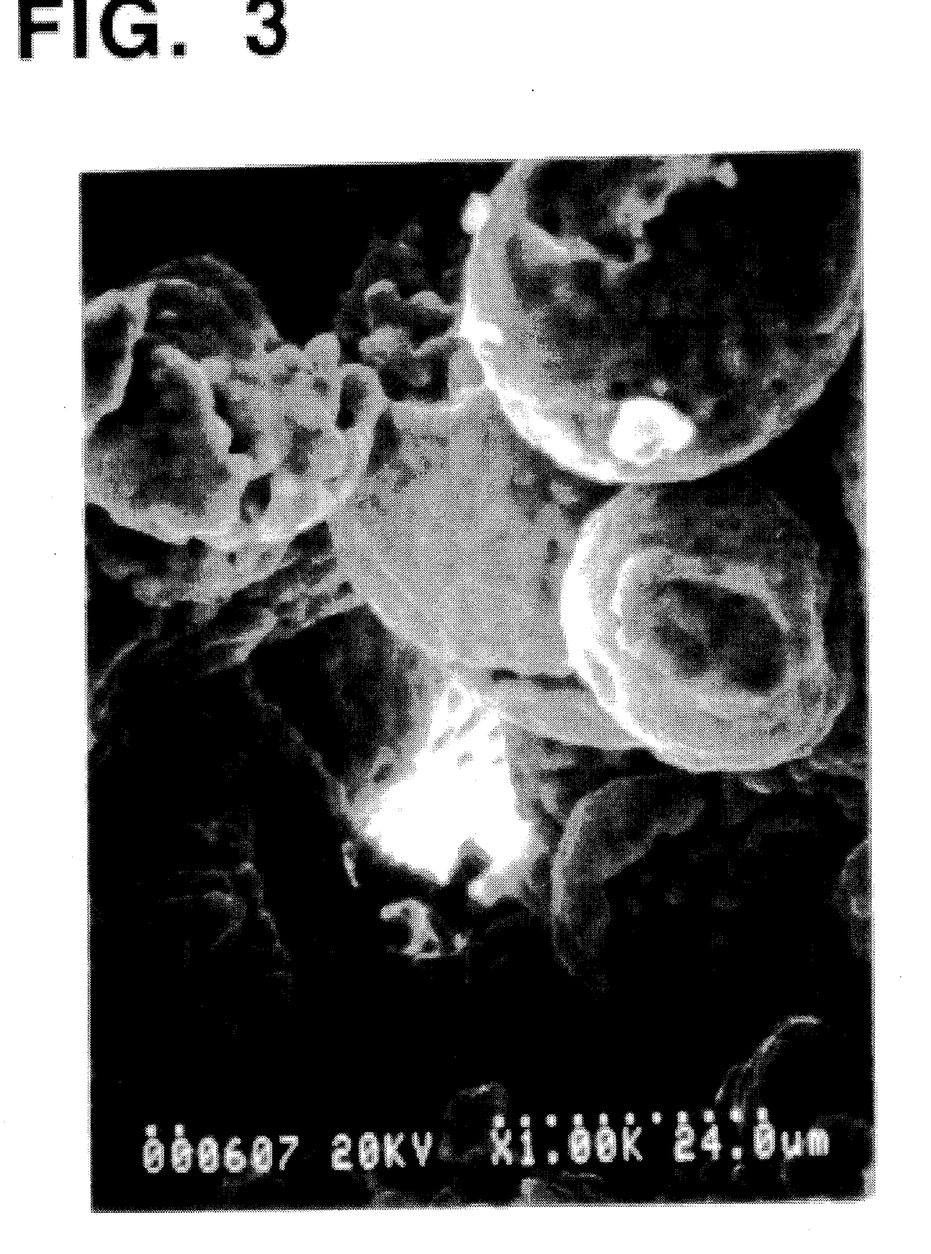
FIGS. 3 and 9 are scanning electron photomicrographs showing the microstructure of a biocompatible implant material (Sample No. 9) obtained in Example 1 according to the present invention.
Figure 4:
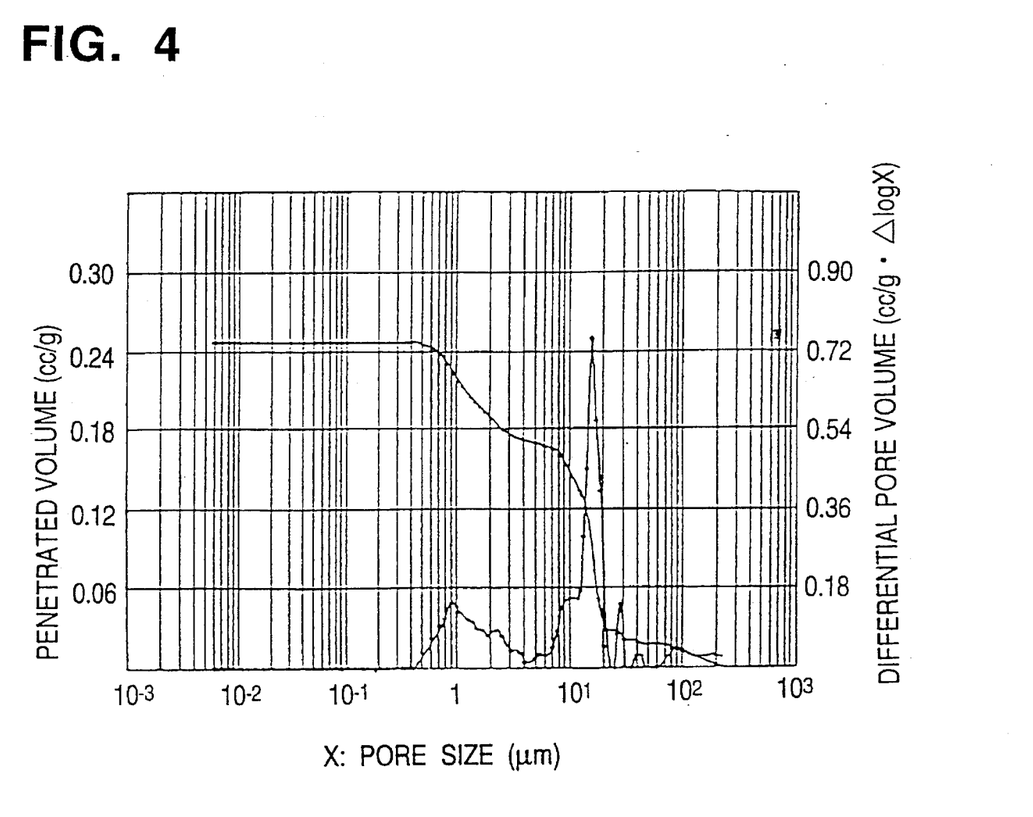
FIG. 4 is a chart showing the pore size distribution for the biocompatible implant material (Sample No. 9) obtained in Example 1 according to the present invention.
Figure 5:
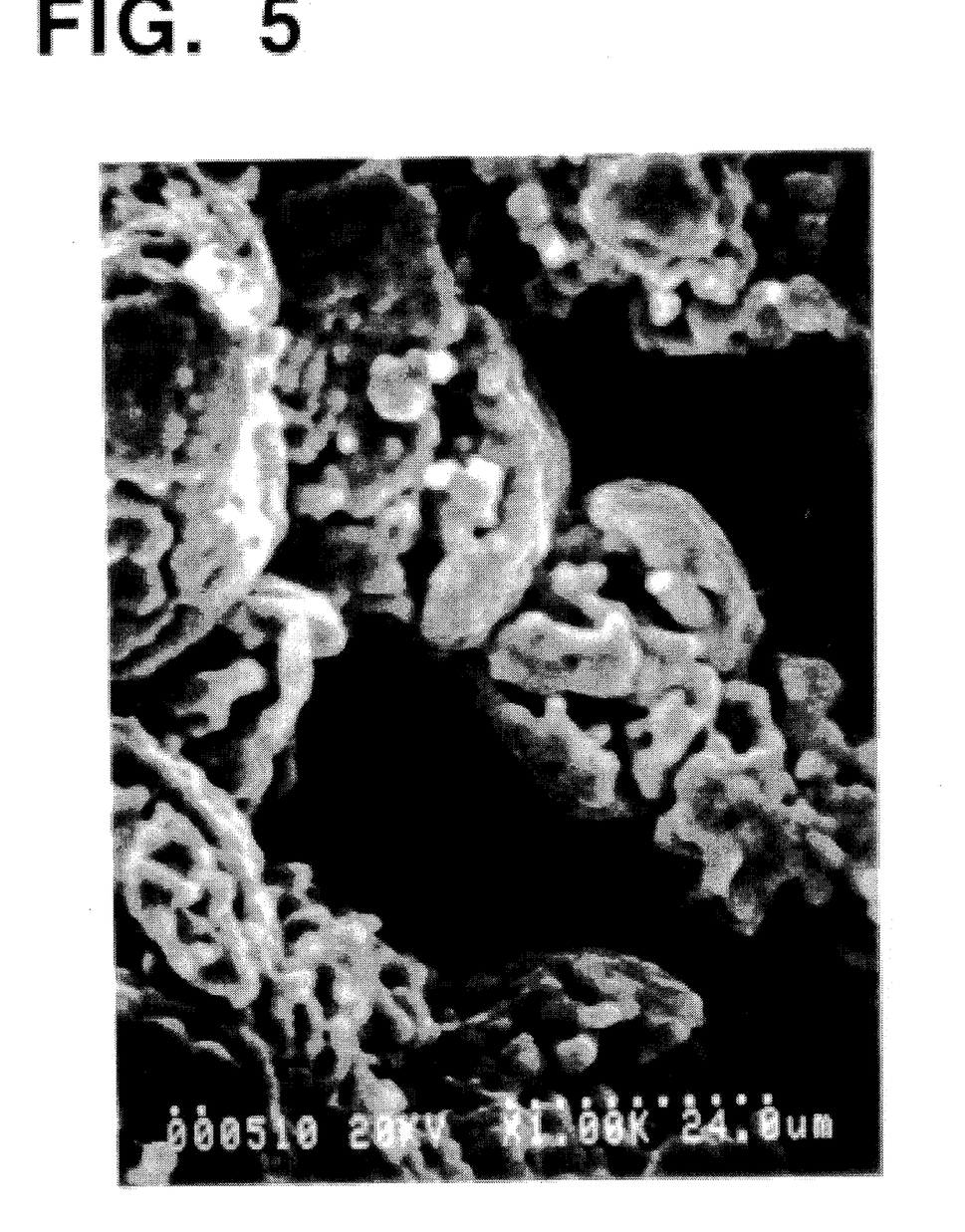
FIG. 5 is a scanning electron photomicrograph showing the microstructure of another biocompatible implant material (Sample No. 15) obtained in Example 1.
Figure 6:
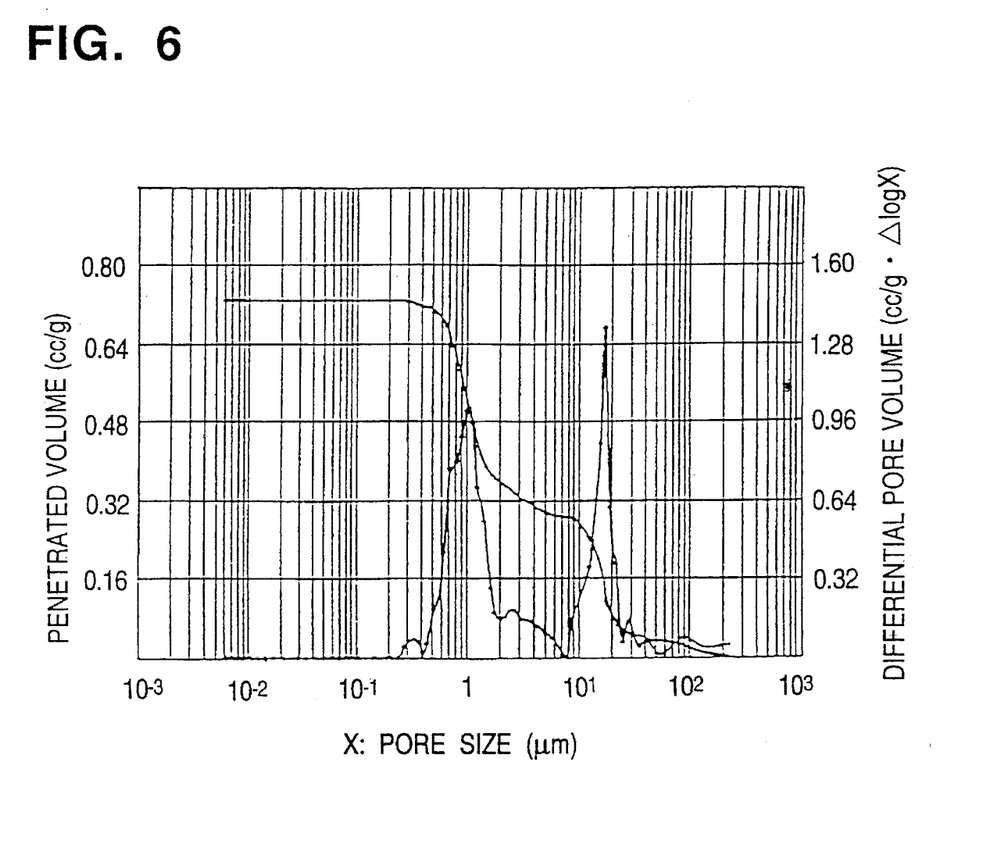
FIG. 6 is a chart showing the pore size distribution for said another biocompatible implant material (Sample No. 15) obtained in Example 1.

In the samples within the scope of the present invention, not only three-dimensionally interconnected pores (open-pore rate>95%) had been formed, but also the pore size distributions as determined by the mercury penetration method showed the presence of satisfactory pores of tens of micrometers or larger. The above results indicate that the interconnected large pores had a particle size of tens of micrometers even at the narrowest parts thereof. Even when the samples were rubbed with, e.g., a finger, falling of particles hardly occurred. Thus, biocompatible implant materials which had high strength and did not break in ordinary handling were obtained. The samples also showed satisfactory machinability. With respect to representative samples, samples Nos. 9 and 15, SEM photographs showing the microstructures thereof are given in FIGS. 3 and 5, respectively, and pore size distributions as determined by the mercury penetration method are given in FIGS. 4 and 6, respectively.

Figure 9:
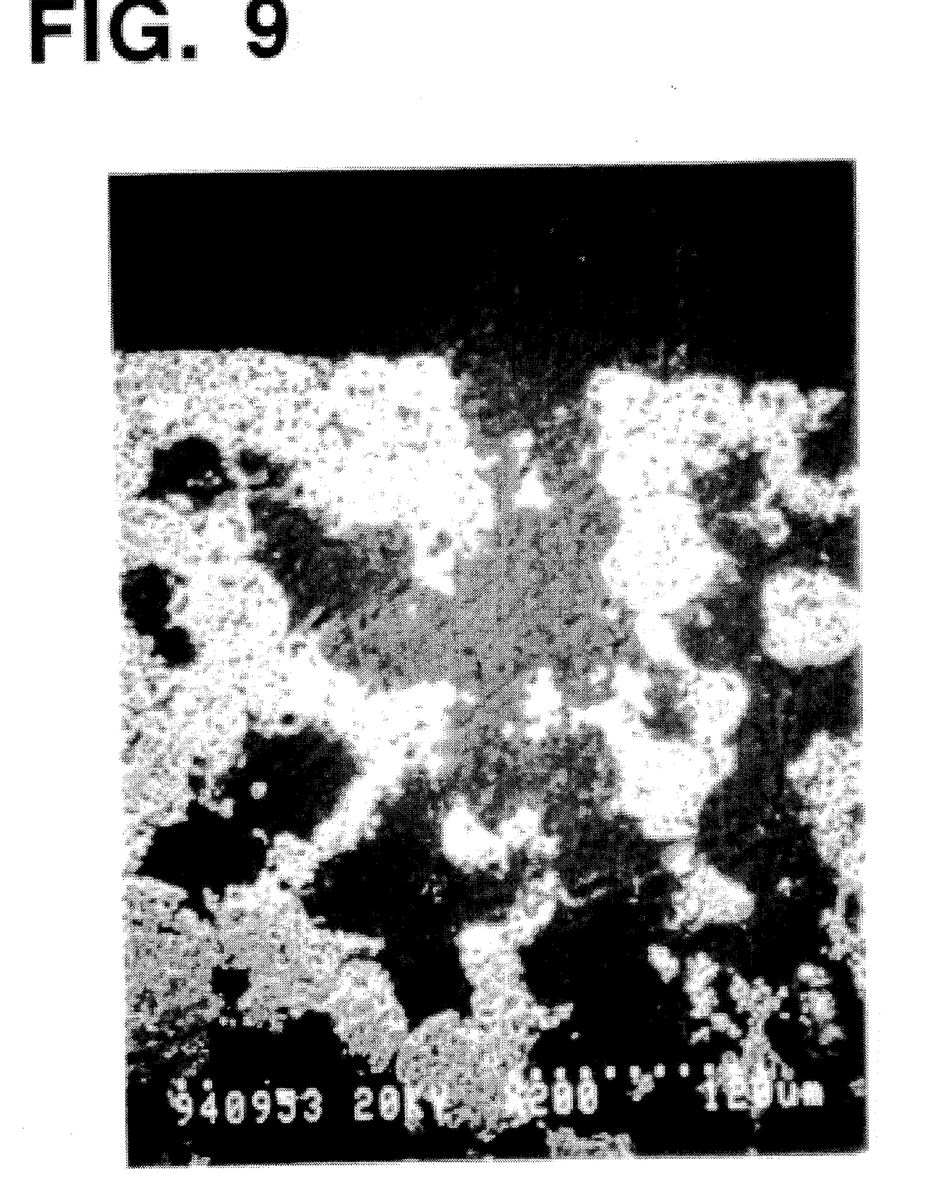

FIG. 9 is another SEM photograph of sample No. 9 showing the connected particle structure having vacant spaces therein comprising three-dimensionally interconnected pores present among particles. The SEM photograph was taken after surface-abrading sample No. 9 which had been impregnated with an organic resin. In FIG. 9, the white parts correspond to calcium phosphate ceramics, and the black parts correspond to the organic resin, that is, correspond to the interconnected pore structure.

The SEM examinations revealed that the samples had a connected-particle structure comprising densely connected spherical calcium phosphate ceramic particles having an average particle size of about 50 μm and that the connected-particle structure had vacant spaces therein comprising three-dimensionally interconnected pores of tens of micrometers. The SEM examinations further revealed that inner parts of the individual ceramic particles of, in particular, the samples fired at 1,100° C. were composed of fine particles bonded together and these individual ceramic particles at least had continuous pores of 2 μm or smaller.

The pore size distributions determined by the mercury penetration method had a characteristic large peak at around 20 μm. Large pores of about 100 μm and minute pores of 2 μm or finer were also detected. These results agreed well with the results of the SEM examinations, showing that the samples were free from the ink bottom effect and the interconnected pores among particles had no narrow parts.

EXAMPLE 2

Using an alumina ceramic raw powder having an average particle size of 1.1 μm, the same procedure as in Example 1 was carried out under the conditions shown in Tables 3 and 4. Thus, samples Nos. 32 to 37 were obtained. It was ascertained that these samples had a connected-particle structure comprising densely bonded spherical alumina ceramic particles having an average particle size of about 20 to 80 μm and the connected-particle structure had vacant spaces therein comprising three-dimensionally interconnected pores of tens of micrometers. As Table 4 shows, these samples had especially good mechanical strength, so that they suffered neither particle falling nor breakage even in rough handling and had high machinability.

EXAMPLE 3

Using a zirconia ceramic raw powder having an average particle size of 0.8 μm, the same procedure as in Example 1 was carried out under the conditions shown in Tables 3 and 4. Thus, samples Nos. 38 to 43 were obtained. It was ascertained that these samples also had a connected-particle structure comprising densely bonded spherical zirconia ceramic particles having an average particle size of about 20 to 80 μm and the connected-particle structure had vacant spaces therein comprising three-dimensionally interconnected pores of tens of micrometers. These samples had especially good mechanical strength as in Example 2, and the machinability thereof was also high.

TABLE 1

| | | Raw Granule | | Combustible Substance | | | |
|---|---|---|---|---|---|---|---|
| Sample | Composition | Raw powder size (μm) | Granule size, S2 (μm) | Particle size, S1 (μm) | S1/S2 | Proportion, vol % | Remarks |
| 1 | Example 1 | calcium phosphate base | 0.6 | 30 | 7 | 0.23 | 40 | the invention |
| 2 | " | " | 0.6 | 30 | 20 | 0.67 | 40 | " |
| 3 | " | " | 0.6 | 30 | 60 | 2 | 40 | " |
| 4 | " | " | 0.6 | 30 | 130 | 4.3 | 40 | " |
| 5 | " | " | 0.6 | 60 | 20 | 0.33 | 40 | " |
| 6 | " | " | 0.6 | 60 | 60 | 1 | 10 | " |
| 7 | " | " | 0.6 | 60 | 60 | 1 | 20 | " |

TABLE 1-continued

| | | Raw Granule | | | Combustible Substance | | | |
| --- | --- | --- | --- | --- | --- | --- | --- | --- |
| Sample | Composition | Raw powder size (μm) | Granule size, S2 (μm) | Particle size, S1 (μm) | S1/S2 | Proportion, vol % | Remarks | |
| 8 | " | " | 0.6 | 60 | 60 | 1 | 30 | " |
| 9 | " | " | 0.6 | 60 | 60 | 1 | 40 | " |
| 10 | " | " | 0.6 | 60 | 60 | 1 | 50 | " |
| 11 | " | " | 0.6 | 60 | 60 | 1 | 60 | " |
| 12 | " | " | 0.6 | 60 | 60 | 1 | 10 | " |
| 13 | " | " | 0.6 | 60 | 60 | 1 | 20 | " |
| 14 | " | " | 0.6 | 60 | 60 | 1 | 30 | " |
| 15 | " | " | 0.6 | 60 | 60 | 1 | 40 | " |
| 16 | " | " | 0.6 | 60 | 60 | 1 | 50 | " |
| 17 | " | " | 0.6 | 60 | 60 | 1 | 60 | " |
| 18 | " | " | 0.6 | 60 | 130 | 2.2 | 40 | " |
| 19 | " | " | 0.6 | 60 | 300 | 5 | 40 | " |
| 20 | " | " | 0.6 | 60 | 60 | 1 | 40 | " |
| 21 | " | " | 0.6 | 60 | 60 | 1 | 40 | " |
| 22 | " | " | 0.6 | 60 | 60 | 1 | 40 | " |
| 23 | " | " | 0.6 | 60 | 60 | 1 | 40 | " |
| 24 | " | " | 0.6 | 60 | 60 | 1 | 40 | " |

TABLE 2

| | | Process | | Property | | | | |
| --- | --- | --- | --- | --- | --- | --- | --- | --- |
| Sample | | Pressing pressure (Kg/cm²) | Firing temperature (°C.) | Porosity (%) | Open-pore rate (%) | Pore structure (mercury penetration method) | | Resistance to particle falling (strength) |
| 1 | Example 1 | 30 | 1300 | 56 | >95 | >3 μm | good | excellent |
| 2 | " | 30 | 1300 | 54 | >95 | >10 μm | excellent | |
| 3 | " | 30 | 1300 | 53 | >95 | >10 μm | " | " |
| 4 | " | 30 | 1300 | 51 | >95 | >10 μm | good | " |
| 5 | " | 30 | 1300 | 54 | >95 | >10 μm | " | " |
| 6 | " | 30 | 1300 | 25 | >90 | >10 μm | excellent | " |
| 7 | " | 30 | 1300 | 34 | >95 | >10 μm | " | " |
| 8 | " | 30 | 1300 | 44 | >95 | >10 μm | " | " |
| 9 | " | 30 | 1300 | 51 | >95 | >10 μm | " | " |
| 10 | " | 30 | 1300 | 59 | >95 | >10 μm | " | good |
| 11 | " | 30 | 1300 | 66 | >95 | >10 μm | " | " |
| 12 | " | 30 | 1100 | 61 | >95 | >10 μm | " | " |
| 13 | " | 30 | 1100 | 66 | >95 | >10 μm | " | " |
| 14 | " | 30 | 1100 | 69 | >95 | >10 μm | " | almost good |
| 15 | " | 30 | 1100 | 74 | >95 | >10 μm | " | " |
| 16 | " | 30 | 1100 | 79 | >95 | >10 μm | " | " |
| 17 | " | 30 | 1100 | 84 | >95 | >10 μm | " | " |
| 18 | " | 30 | 1300 | 50 | >95 | >10 μm | good | good |
| 19 | " | 30 | 1300 | 54 | >95 | >10 μm | " | " |
| 20 | " | 3.5 | 1300 | 67 | >95 | >10 μm | " | almost good |
| 21 | " | 5 | 1300 | 65 | >95 | >10 μm | " | " |
| 22 | " | 15 | 1300 | 62 | >95 | >10 μm | " | good |
| 23 | " | 50 | 1300 | 50 | >95 | >10 μm | " | excellent |
| 24 | " | 100 | 1300 | 46 | >95 | >10 μm | " | " |

TABLE 3

| | | Raw Granule | | | Combustible Substance | | | |
| --- | --- | --- | --- | --- | --- | --- | --- | --- |
| Sample | Composition | Raw powder size (μm) | size, S2 (μm) | size, S1 (μm) | S1/S2 | Proportion, vol % | Remarks | |
| 25 | Example 1 | calcium phosphate base | 0.6 | 90 | 20 | 0.22 | 40 | the invention |
| 26 | " | " | 0.6 | 90 | 60 | 0.67 | 40 | " |
| 27 | " | " | 0.6 | 90 | 130 | 1.44 | 40 | " |
| 28 | " | " | 0.6 | 90 | 300 | 3.3 | 40 | " |

TABLE 3-continued

| Sample | Raw Granule | | | Combustible Substance | | | Remarks |
|---|---|---|---|---|---|---|---|
| | Composition | Raw powder size (μm) | size, S2 (μm) | size, S1 (μm) | S1/S2 | Proportion, vol % | |
| 29 | " | " | 0.6 | 300 | 60 | 0.2 | 40 | " |
| 30 | " | " | 0.6 | 300 | 130 | 0.43 | 40 | " |
| 31 | " | " | 0.6 | 300 | 300 | 1 | 40 | " |
| 32 | Example 2 | alumina base | 1.1 | 30 | 60 | 2 | 30 | " |
| 33 | " | " | 1.1 | 30 | 60 | 2 | 50 | " |
| 34 | " | " | 1.1 | 60 | 60 | 1 | 30 | " |
| 35 | " | " | 1.1 | 60 | 60 | 1 | 50 | " |
| 36 | " | " | 1.1 | 90 | 60 | 0.67 | 30 | " |
| 37 | " | " | 1.1 | 90 | 60 | 0.67 | 50 | " |
| 38 | Example 3 | zirconia base | 0.8 | 30 | 60 | 2 | 30 | " |
| 39 | " | " | 0.8 | 30 | 60 | 2 | 50 | " |
| 40 | " | " | 0.8 | 60 | 60 | 1 | 30 | " |
| 41 | " | " | 0.8 | 60 | 60 | 1 | 50 | " |
| 42 | " | " | 0.8 | 90 | 60 | 0.67 | 30 | " |
| 43 | " | " | 0.8 | 90 | 60 | 0.67 | 50 | " |

TABLE 4

| Sample | Process | | Property | | | | Resistance to particle falling (strength) |
|---|---|---|---|---|---|---|---|
| | Pressing pressure (Kg/cm$^2$) | Firing temperature (°C.) | Porosity (%) | Open-pore rate (%) | Pore structure (mercury penetration method) | | |
| 25 Example 1 | 30 | 1300 | 53 | >95 | >10 μm | good | good |
| 26 " | 30 | 1300 | 51 | >95 | >10 μm | excellent | " |
| 27 " | 30 | 1300 | 52 | >95 | >10 μm | " | almost good |
| 28 " | 30 | 1300 | 53 | >95 | >10 μm | good | " |
| 29 " | 30 | 1300 | 53 | >95 | >10 μm | " | " |
| 30 " | 30 | 1300 | 52 | >95 | >10 μm | excellent | " |
| 31 " | 30 | 1300 | 51 | >95 | >10 μm | " | " |
| 32 Example 2 | 60 | 1600 | 43 | >95 | >10 μm | " | excellent |
| 33 " | 60 | 1600 | 58 | >95 | >10 μm | " | " |
| 34 " | 60 | 1600 | 44 | >95 | >10 μm | " | " |
| 35 " | 60 | 1600 | 59 | >95 | >10 μm | " | " |
| 36 " | 60 | 1600 | 46 | >95 | >10 μm | " | " |
| 37 " | 60 | 1600 | 60 | >95 | >10 μm | " | " |
| 38 Example 3 | 90 | 1450 | 42 | >95 | >10 μm | " | " |
| 39 " | 90 | 1450 | 56 | >95 | >10 μm | " | " |
| 40 " | 90 | 1450 | 43 | >95 | >10 μm | " | " |
| 41 " | 90 | 1450 | 57 | >95 | >10 μm | " | " |
| 42 " | 90 | 1450 | 44 | >95 | >10 μm | " | " |
| 43 " | 90 | 1450 | 59 | >95 | >10 μm | " | " |

COMPARATIVE EXAMPLE 1

As is shown in Tables 5 and 6, the same powder mixture as that used in Example 1, which consisted of a hydroxyapatite powder and 5 wt % of calcium phosphate glass frit, was employed as a raw powder and mixed with a spherical acrylic combustible substance without being granulated with a spray dryer. Thereto was added 3 wt % of an acrylic binder. The resulting mixture was pressed with a mold press at a pressure of 800 kg/cm$^2$, and the pressed shape was fired. Thus, samples Nos. 44 to 49 were obtained. Some of these samples had a high porosity, and large pores of tens of micrometers were observed in an SEM examination (FIG. 7). However, a measurement by the mercury penetration method (FIG. 8) detected only pores of 1 μm or smaller. The above results indicate that in these samples, large pores were narrowly interconnected through point contact parts which were as narrow as about 1 μm.

COMPARATIVE EXAMPLE 2

The same raw powder as in Example 1 was used but the pressing was conducted at pressures of 0.5 kg/cm$^2$ and 200 kg/cm$^2$ as shown in Tables 5 and 6. Thus, samples Nos. 50 to 53 were obtained. In the case of pressing at 0.5 kg/cm$^2$ (samples Nos. 50 and 51), the sintered body obtained could not retain the shape and were not handleable. In the case of pressing at 200 kg/cm$^2$ (samples Nos. 52 and 53), only pores of 1 μm or smaller were detected in a measurement by the mercury penetration method.

COMPARATIVE EXAMPLE 3

The same procedure as in Example 1 was carried out except that no combustible substances were added, as shown in Tables 5 and 6. Thus, samples Nos. 54 and 55 were obtained. In these samples, only pores of 5 μm or smaller were detected in a measurement by the mercury penetration method.

COMPARATIVE EXAMPLE 4

The same procedure as in Example 1 was carried out except that the ratio of the average particle size (S1) of the combustible substance to the average particle size (S2) of the raw granules (S1/S2) was changed to values not larger than 0.2 or not smaller than 5, as shown in Tables 5 and 6. Thus, samples Nos. 56 to 65 were obtained. In these samples, only pores of 5 μm or smaller were detected in a measurement by the mercury penetration method. Further, in the case of the raw materials for samples Nos. 56 and 57, into which a combustible substance having a particle size of 1.5 μm had been added, uniform mixing was difficult and the resulting sintered bodies had large voids and cracks.

COMPARATIVE EXAMPLE 5

The same procedure as in Example 1 was carried out except that a hydroxyapatite powder having an average particle size of 8.8 μm was used as a starting material, as shown in Tables 5 and 6. Thus, samples Nos. 66 and 67 were obtained. In these samples, neck growth during firing had been insufficient. These samples had developed cracks through firing, and were so fragile that breakage readily occurred upon touching with a finger.

COMPARATIVE EXAMPLE 6

As Tables 5 and 6 show, the same powder mixture as that used in Example 1, which consisted of a hydroxyapatite powder and 5 wt % of calcium phosphate glass frit, was mixed as a raw powder with 3 wt % of acrylic binder, and the resulting mixture was pressed at a pressure of 800 kg/cm$^2$. This pressed body was crushed and classified by screening to prepare raw granules having an average particle size of 1,200 μm. The raw granules were mixed with a spherical acrylic combustible substance. The resulting mixture was treated in the same manner as in Example 1. Thus, samples Nos. 68 and 69 were obtained. In these samples, neck growth during firing had been insufficient. These samples had developed cracks through firing, and were so fragile that breakage readily occurred upon touching with a finger.

TABLE 5

| Sample | | Raw Granule | | | Combustible Substance | | | Remarks |
|---|---|---|---|---|---|---|---|---|
| | Composition | Raw powder size (μm) | size, S2 (μm) | size, S1 (μm) | S1/S2 | Proportion, vol % | | |
| 44 | Comparative Example 1 | calcium phosphate base | 0.6 | not granulated | 60 | — | 20 | Comparative Example |
| 45 | Comparative Example 1 | " | 0.6 | " | 60 | — | 40 | " |
| 46 | Comparative Example 1 | " | 0.6 | " | 60 | — | 60 | " |
| 47 | Comparative Example 1 | " | 0.6 | " | 60 | — | 20 | " |
| 48 | Comparative Example 1 | " | 0.6 | " | 60 | — | 40 | " |
| 49 | Comparative Example 1 | " | 0.6 | " | 60 | — | 60 | " |
| 50 | Comparative Example 2 | " | 0.6 | 60 | 60 | 1 | 40 | " |
| 51 | Comparative Example 2 | " | 0.6 | 60 | 60 | 1 | 40 | " |
| 52 | Comparative Example 2 | " | 0.6 | 60 | 60 | 1 | 40 | " |
| 53 | Comparative Example 2 | " | 0.6 | 60 | 60 | 1 | 40 | " |
| 54 | Comparative Example 3 | " | 0.6 | 60 | none | — | — | " |
| 55 | Comparative Example 3 | " | 0.6 | 60 | none | — | — | " |
| 56 | Comparative Example 4 | calcium phosphate base | 0.6 | 30 | 1.5 | 0.07 | 40 | Comparative Example |
| 57 | Comparative Example 4 | " | 0.6 | 30 | 1.5 | 0.07 | 40 | " |
| 58 | Comparative Example 4 | " | 0.6 | 30 | 300 | 10 | 40 | " |
| 59 | Comparative Example 4 | " | 0.6 | 30 | 300 | 10 | 40 | " |
| 60 | Comparative Example 4 | " | 0.6 | 60 | 7 | 0.12 | 40 | " |
| 61 | Comparative Example 4 | " | 0.6 | 60 | 7 | 0.12 | 40 | " |
| 62 | Comparative Example 4 | " | 0.6 | 90 | 7 | 0.08 | 40 | " |
| 63 | Comparative Example 4 | " | 0.6 | 90 | 7 | 0.08 | 40 | " |
| 64 | Comparative Example 4 | " | 0.6 | 300 | 7 | 0.02 | 40 | " |
| 65 | Comparative Example 4 | " | 0.6 | 300 | 7 | 0.02 | 40 | " |
| 66 | Comparative Example 5 | " | 8.8 | 60 | 60 | 1 | 40 | " |
| 67 | Comparative | " | 8.8 | 60 | 60 | 1 | 40 | " |

TABLE 5-continued

| | Sample | Raw Granule Composition | Raw powder size (μm) | size, S2 (μm) | Combustible Substance size, S1 (μm) | S1/S2 | Proportion, vol % | Remarks |
|---|---|---|---|---|---|---|---|---|
| 68 | Example 5 Comparative Example 6 | " | 0.6 | 1200 | 300 | 0.25 | 40 | " |
| 69 | Comparative Example 6 | " | 0.6 | 1200 | 300 | 0.25 | 40 | " |

TABLE 6

| | Sample | Process Pressing pressure (Kg/cm²) | Firing temperature (°C.) | Property Porosity (%) | Open-pore rate (%) | Pore structure (mercury penetration method) | | Resistance to particle falling (strength) |
|---|---|---|---|---|---|---|---|---|
| 44 | Comparative Example 1 | 800 | 1300 | 21 | 45 | <1 μm | poor | excellent |
| 45 | " | 800 | 1300 | 42 | 68 | <1 μm | " | " |
| 46 | " | 800 | 1300 | 59 | 81 | <1 μm | " | good |
| 47 | " | 800 | 1100 | 53 | >85 | <1 μm | " | " |
| 48 | " | 800 | 1100 | 61 | >85 | <1 μm | " | " |
| 49 | " | 800 | 1100 | 71 | >85 | <1 μm | " | almost good |
| 50 | Comparative Example 2 | 0.5 | 1300 | | | unable to retain the shape | | |
| 51 | " | 0.5 | 1100 | | | " | | |
| 52 | " | 200 | 1300 | 43 | >95 | <1 μm | poor | good |
| 53 | " | 200 | 1100 | 63 | >95 | <1 μm | " | " |
| 54 | Comparative Example 3 | 30 | 1300 | 34 | >90 | <5 μm | " | " |
| 55 | " | 30 | 1100 | 65 | >95 | <5 μm | " | " |
| 56 | Comparative Example 4 | 30 | 1300 | | | insufficient mixing, cracked | | |
| 57 | " | 30 | 1100 | | | " | | |
| 58 | " | 30 | 1300 | 44 | >95 | <5 μm | poor | poor |
| 59 | " | 30 | 1100 | 63 | >95 | <5 μm | " | " |
| 60 | " | 30 | 1300 | 37 | >95 | <1 μm | " | good |
| 61 | " | 30 | 1100 | 56 | >95 | <1 μm | " | " |
| 62 | " | 30 | 1300 | 38 | >95 | <1 μm | " | " |
| 63 | " | 30 | 1100 | 58 | >95 | <1 μm | " | " |
| 64 | " | 30 | 1300 | 37 | >95 | <1 μm | " | poor |
| 65 | " | 30 | 1100 | 57 | >95 | <1 μm | " | " |
| 66 | Comparative Example 5 | 30 | 1300 | | | fragile, cracked | | |
| 67 | " | 30 | 1100 | | | " | | |
| 68 | Comparative Example 6 | 50 | 1300 | | | " | | |
| 69 | " | 50 | 1100 | | | " | | |

As described above, the biocompatible implant material of the present invention has an advantage that after it is implanted, a body fluid penetrates very easily into vacant parts of the implant material and the growth of a new bone is accelerated, because the implant material has a pore structure having vacant spaces comprising three-dimensionally interconnected pores present among particles of a connected-particle structure and having a pore size of 2 to 800 μm, and because no extremely narrow parts with a pore size below 2 μm are present at the joint parts between such pores. Thus, the implant material of this invention can exhibit high biocompatibility with excellent bone tissue penetration.

Even when having a porosity as high as 50 to 80%, the biocompatible implant material of the present invention can be easily implanted in a living body because it has so high mechanical strength that it neither suffers particle falling or the like upon touching with the hand nor is crushed with fingers, etc. In particular, in the case where the implant material was one produced from a raw powder comprising a mixture of a hydroxyapatite powder and a calcium phosphate glass powder, it had so high mechanical strength that it neither suffered particle falling or the like upon touching with the hand nor was crushed with fingers, etc., even when it had a porosity as high as 40 to 70 vol %. In wet processing using a diamond grinder, the implant material could be satisfactorily machined without readily suffering breakage.

According to the process of the present invention for producing a biocompatible implant material, a porous object having the pore structure described above can be efficiently produced with ease.

The biocompatible implant material of the present invention is also useful as a biocompatible implant material for a drug delivery system (DDS) because it is also excellent in drug retention due to the fine continuous voids present within the particles thereof.

While the invention has been described in detail and with reference to specific embodiments thereof, it will be apparent to one skilled in the art that various changes and modifications can be made therein without departing from the spirit and scope thereof.

What is claimed is:

1. A process for producing a biocompatible implant material which comprises granulating a raw powder having an average particle size of 5 μm or smaller to give raw granules having an average particle size 10 to 800 μm, mixing said raw granules with a combustible substance having an average particle size of 2 to 1,600 μm, pressing the mixture into a shape at a pressure of 1 to 100 kg/cm², and then firing said shape.

2. The process as claimed in claim 1, wherein said raw granules and the particles of said combustible substance are nearly spherical.

3. The process as claimed in claim 2, wherein said raw granules are spherical granules prepared by using a spray dryer, and said combustible substance is acrylic or polystyrene organic beads.

4. The process as claimed in claim 2, wherein said raw granules have an average particle size of 30 to 300 μm, and said combustible substance has an average particle size of 20 to 300 μm.

5. The process as claimed in claim 4, wherein the particle size distribution is such that a portion of the raw granules having a particle size of ½ to 2 times that of the average particle size of all the raw granules account for 80% or more of all the raw granules, and a portion of the combustible substance having a particle size of ½ to 2 times that of the average particle size of all the combustible substance accounts for 80% or more of all the combustible substance.

6. The process as claimed in claim 1, wherein the ratio of the average particle size (S1) of the combustible substance to the average particle size (S2) of the raw granules, S1/S2, is from 0.2 to 5.

7. The process as claimed in claim 1, wherein said raw granules are made of a mixture of a crystalline ceramic powder and a crystalline or glass powder which generates a liquid phase during firing.

8. The process as claimed in claim 1, wherein said raw granules are made of a material selected from the group consisting of alumina ceramics, zirconia ceramics, and alumina-zirconia ceramics.

9. The process as claimed in claims 1, wherein said raw granules are made of a material comprising calcium phosphate ceramics.

10. The process as claimed in claim 9, wherein said raw granules are made of a mixture of a hydroxyapatite powder and a calcium phosphate glass powder.

* * * * *